United States Patent [19]

Schäfer et al.

[11] 4,344,855

[45] Aug. 17, 1982

[54] PROCESS FOR THE PRODUCTION OF POLYISOCYANATES WHICH CONTAIN CARBODIIMIDE GROUPS AND WHICH ARE STABLE IN STORAGE

[75] Inventors: Walter Schäfer, Cologne; Kuno Wagner, Leverkusen; Hans-Dieter Block, Cologne, all of Fed. Rep. of Germany

[73] Assignee: Bayer Aktiengesellschaft, Leverkusen, Fed. Rep. of Germany

[21] Appl. No.: 741,432

[22] Filed: Nov. 12, 1976

[30] Foreign Application Priority Data

Nov. 21, 1975 [DE] Fed. Rep. of Germany ....... 2552350

[51] Int. Cl.³ .............................................. C09K 3/00
[52] U.S. Cl. ..................................... 252/182; 528/51; 528/67; 521/107; 521/901
[58] Field of Search ................... 252/182; 528/51, 67; 521/DIG. 901, 107; 260/453 A, 453 P

[56] References Cited

U.S. PATENT DOCUMENTS

| | | | |
|---|---|---|---|
| 3,676,402 | 7/1972 | Matsui et al. | 528/45 |
| 3,887,476 | 6/1975 | McConnell | 548/349 |
| 3,952,084 | 4/1976 | Edelman et al. | 252/182 |
| 3,953,406 | 4/1976 | Marsh | 252/182 |
| 4,046,744 | 9/1977 | Jenkins | 528/51 |

FOREIGN PATENT DOCUMENTS 918454   2/1963   United Kingdom ................ 252/182

*Primary Examiner*—J. L. Barr
*Attorney, Agent, or Firm*—Gene Harsh; Joseph C. Gil

[57] ABSTRACT

The instant invention relates to a process for producing stable equilibrium mixtures of carbodiimides, uretone imines and organic isocyanates and storage-stable solutions of carbodiimides and uretone imines in polyisocyanates which are free from carbodiimide groups. Either the carbodiimide, or the uretone imine, or both, may contain isocyanate groups. The invention relates to the process for the preparation of these products by so-called heterogeneous catalysis and the use of these products for the production of polyurethane resins.

10 Claims, No Drawings

PROCESS FOR THE PRODUCTION OF POLYISOCYANATES WHICH CONTAIN CARBODIIMIDE GROUPS AND WHICH ARE STABLE IN STORAGE

BACKGROUND OF THE INVENTION

Carbodiimides can be obtained by a very simple reaction from isocyanates even at room temperature according to the basic procedure described in German Pat. No. 1,130,594, using phospholine oxides as catalysts. Commercially, the most important and effective catalysts which are capable of effecting very rapid carbodiimidization of aromatic monoisocyanates and polyisocyanates even at room temperature and of converting less reactive aliphatic and cycloaliphatic monoisocyanates and polyisocyanates into carbodiimides at temperatures upwards of about 150° C. are those of the general formulae

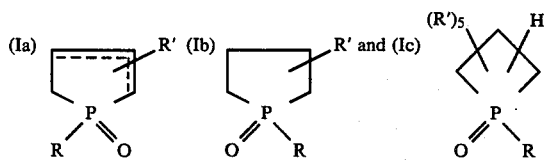

in which R and R' represents aromatic or aliphatic hydrocarbon groups having from 1 to 14, and preferably 1 to 4 carbon atoms and R' may also represent a hydrogen atom.

Catalysts of this kind have already been used industrially for the production of polycarbodiimide foams [relative to compounds (1c) see J. org. Chemistry 32, 4066 (1967)].

Experience has shown that the formation of carbodiimides taking place in a homogeneous phase with the aid of the aforesaid readily soluble catalysts cannot be stopped at the stage necessary to obtain high quality isocyanate-containing carbodiimides or polycarbodiimides which are stable in storage. It is likewise not possible to prepare stable solutions of diisocyanato-carbodiimides or α,ω-diisocyanato-bis-carbodiimides or α,ω-diisocyanato-tris-carbodiimides or the isocyanato-uretoneimines (obtained from these products by the reaction between carbodiimide and isocyanate groups) such as those corresponding to the formula

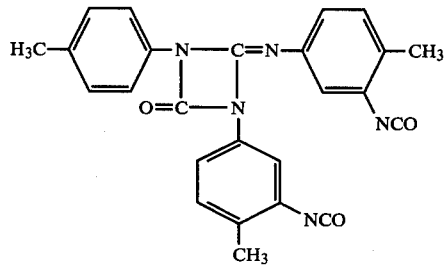

in excess monomeric monoisocyanates or polyisocyanates. Carbodiimidization taking place under the influence of catalytically highly active soluble phospholine oxides is practically impossible to stop with inactivating agents such as phosphorus oxychloride, zinc chloride, dimethyl carbamic acid chloride, benzoyl chloride, hydrochloric acid, boron trifluoride, alkylating agents and the like. Consequently, inferior high molecular weight insoluble products are produced. Because of the progressive (although slow) formation of carbodiimides, a high carbon dioxide pressure soon builds up inside closed vessels, which may cause serious accidents.

DESCRIPTION OF THE INVENTION

It has now surprisingly been found that it is possible to bind carbodiimidization catalysts by covalent bonds to or in a high molecular weight organic matrix which is capable of swelling but is insoluble in polyisocyanates without thereby significantly reducing the activity of the catalysts. The catalysts obtained in this way are high molecular weight, insoluble products capable of swelling which can be removed from the reaction mixture whenever desired so that it becomes possible to convert monoisocyanates and, preferably, polyisocyanates into products which are stable in storage consisting or carbodiimides or polycarbodiimides and their uretoneimines containing functional isocyanate groups and/or mixtures of (poly)carbodiimides and their uretoneimines with polyisocyanates.

The present invention therefore relates to a process for the preparation of storage-stable catalyst-free mixtures of mono and/or polyisocyanates which may be only partially carbodiimidized and which may still contain mono- and/or polyisocyanates which are free from carbodiimide groups, which process is characterized in that mono- and/or polyisocyanates are brought into contact with high molecular weight carbodiimidization catalysts which are insoluble in polyisocyanates and which consist of a high molecular weight matrix and of a low molecular weight carbodiimidization catalyst which is covalently bound to the matrix, (the said catalyst being preferably a saturated or unsaturated 5-membered or saturated 4-membered cyclic phosphine oxide); the high molecular weight, insoluble catalyst is removed when the required degree of carbodiimidization has been reached. If desired mono- and/or polyisocyanates which are free from carbodiimide groups can be subsequently added.

The molecular weight of the organic matrix used according to the invention is generally above 2000. Highly cross-linked products are preferably used according to the invention.

Any known low molecular weight carbodiimidization catalysts or precursors thereof which are converted into the catalytically active form only when built into the matrix may, in principle, be used for preparing the high molecular weight carbodiimidization catalysts used according to the invention. In order to be able to build the known low molecular weight carbodiimidization catalysts into the high molecular weight matrix, it may in some cases be necessary to modify the catalysts with functional groups which are capable of reacting with functional groups of the matrix or with the monomers used for producing the matrix.

The low molecular weight carbodiimidization catalyst and high molecular weight matrix may be linked through any covalent bonds, e.g. carbon-carbon bonds, ether, ester, urethane, amide, sulphide groups, and the like. Ester groups are preferred according to the invention, with aliphatic carbon-carbon bonds being particularly preferred.

Particularly preferred low molecular weight carbodiimidization catalysts for preparing the high molecular weight carbodiimidization catalysts used in the process according to the invention are cyclic phosphine oxides of the type described above (Formula Ia) and derivatives thereof in the form of cyclic phosphine oxides in which the ring may, in addition, carry substituents with functional groups for linking the covalent bonds.

Another preferred type of compound for preparing the high molecular weight carbodiimidization catalysts used in the process according to the invention are cyclic phosphine oxides which are derived from compounds of the general formula (Ib) but contain alkyl, aryl or aralkyl substituents with functional groups on the ring or on the phosphorus atom or have functional groups directly attached to the ring, these functional groups serving to form covalent bonds through which the phosphine oxides can be linked to the polymer matrix.

Compounds of this kind include, for example, those of the following general formulae:

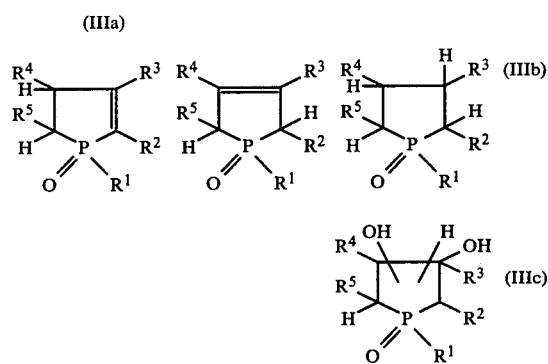

in which
R$^1$ represents halogen, an alkoxy group, an aryloxy group having up to 14 carbon atoms or an amino group which may be substituted with alkyl, alkenyl, aryl or aralkyl groups having up to 14 carbon atoms, or it may represent an alkyl, alkenyl, aryl or aralkyl group having up to 14, preferably 1 to 4 carbon atoms, and may also contain amino or hydroxy groups, and
R$^2$, R$^3$, R$^4$ and R$^5$ represent hydrogen, halogen, a carboxyl group, C$_1$-C$_{14}$ and preferably C$_1$ to C$_4$-alkyl or alkoxy carbonyl groups, phosphonic acid ester groups or C$_1$ to C$_4$ alkoxy or alkylmercapto groups which may in addition contain functional groups such as olefinic carbon-to-carbon double bonds or amino or hydroxyl groups.

The following are typical representatives of such compounds:

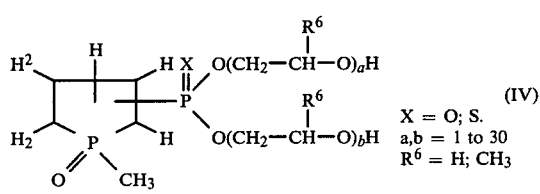

or

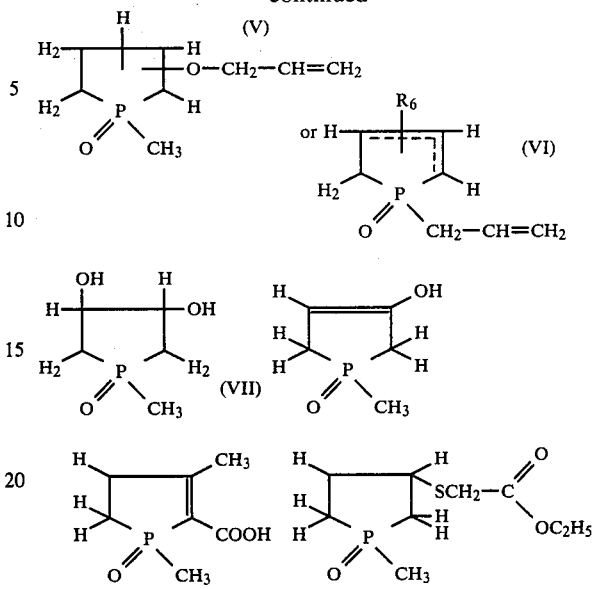

Low molecular weight catalysts of this kind may be prepared as follows:

Compounds of type (IV) by reaction of a compound of the formula

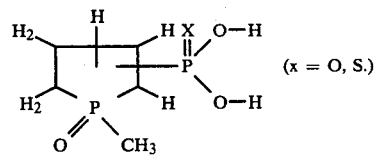

with ethylene oxide or propylene oxide. The reaction is carried out at from 0° to 180° C., preferably 50° to 150° C., either at normal pressure or at elevated pressure and, if desired, in an inert solvent.

Low molecular weight carbodiimidization catalysts of type (IV) which are alkyl substituted on the phospholane ring may be prepared in a similar manner as described in German Offenlegungsschrift No. 2,504,400.

Compounds of the formula (V) may be obtained by reaction of compounds of the general formula

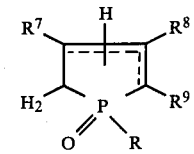

in which
R represents an alkyl or an aryl group having up to 14 carbon atoms and
R$^7$, R$^8$ and R$^9$ which may be the same or different represent C$_1$-C$_4$-alkyl group or hydrogen with a compound of the general formula R$^{10}$—O—H
in which
R$^{10}$ represents an alkyl, aryl or aralkyl group having from 1 to 14, preferably 1 to 4 carbon atoms which may in addition contain functional groups such as olefinic carbon to carbon double bonds
in the presence of alkaline catalysts.

Compounds of the formula (VI) may be obtained by reacting compounds of the general formula

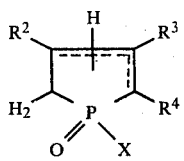

[Izvestiya Akademii NaukSSSR, Seriya Khimicheskaya, No. 8, pp. 1847–1848 (other there)]

in which

X represents a halogen atom, e.g. chlorine, bromine or iodine and $R^2$, $R^3$ and $R^4$ which may be the same or different and represent a $C_1$ to $C_4$-alkyl group or hydrogen with an organometallic compound, e.g. a Grignard compound, in which the organic group may contain the desired functional groups such as olefinic C=C double bonds. Solvents such as hydrocarbons and ethers (THF), for example, may be used for this reaction.

Compounds of the formula (VII) are obtained by hydrolysis of 3,4-epoxyphospholan-1-oxides [A. Arbusov, A. P. Rakow, A. O. Vizel, Izv. Akad, Nauk SSSR, 1969 2230–2234)].

The phosphorus content of the high molecular weight catalysts used according to the invention which are based on compounds of formula (I) or (III) is generally between 0.05 and 23% by weight, preferably between 0.3 and 8% by weight.

The so-called precursors of low molecular weight carbodiimidization catalysts used according to the invention may be, for example, compounds of the general formula

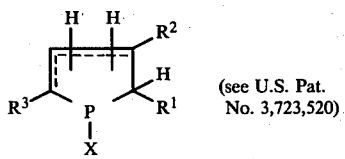 (VIII)

(see U.S. Pat. No. 3,723,520)

in which $R^1$, $R^2$ and $R^3$ represent hydrogen or $C_1$–$C_{14}$-preferably $C_1$–$C_4$-alkyl groups and X represents halogen.

Compounds of this kind can be built into a high molecular weight matrix to form the catalytically active cyclic phosphine oxide group, for example as illustrated in the following reaction scheme:

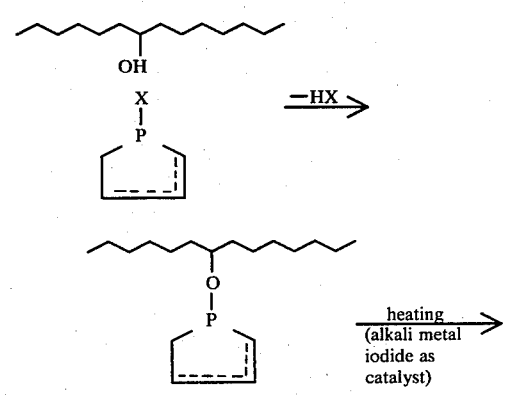 (IX)

The Arbusov reaction is another possibility:

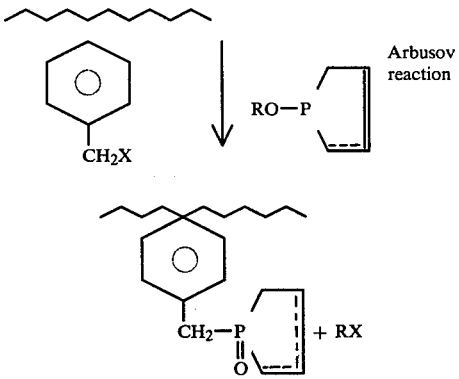

Arbusov reaction

Other "precursors" of carbodiimidization catalysts include, for example, compounds of the formula R—$PX_2$ (X=halogen), wherein the group $PX_2$ is attached to an alkyl, aryl or aralkyl group which may already be part of a high polymer. Examples of such compounds include the reaction products of $PX_3$ with polystyrene.

Compounds of the formula R—$PX_2$ can readily be converted into cyclic phosphine oxides by reaction with dienes, followed by hydrolysis as represented by the following reaction scheme:

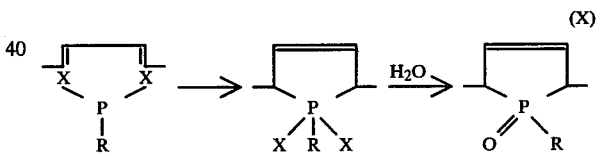 (X)

The basic high molecular weight structure for the catalysts used in the process according to the invention may consist of polymers which contain functional groups for a covalent linkage with the low molecular weight carbodiimidization catalyst. Alternatively, the high molecular weight catalysts may, of course, also be prepared from monomers which during their polymerization to high molecular weight products build into their structure the low molecular weight carbodiimidization catalyst containing suitable functional groups.

A preferred matrix for catalysts used in the process according to the invention is one consisting of unsaturated polyester resins. When such a matrix is used, dicarboxylic acids and diols, at least one of which is unsaturated, are first condensed by known methods to produce an unsaturated polyester. About 10 to 70% by weight (based on the polyester) of a phospholine oxide which may contain a substituent with an additional olefinic double bond are then added and the mixture is heated, together with reaction initiators.

Instead of free dicarboxylic acids, the corresponding dicarboxylic acid anhydrides or corresponding carboxylic acid esters of lower alcohols or mixtures thereof may be used for preparing the polyesters. The carboxylic acids used may be aliphatic, cycloaliphatic, aromatic and/or heterocyclic and they may be substituted, for example with halogen atoms. The following are examples: Malonic acid; succinic acid; adipic acid; suberic acid; azelaic acid; sebacic acid; phthalic acid; isophthalic acid; trimellitic acid; phthalic acid anhydride; tetrahydrophthalic acid anhydride; hexahydrophthalic acid anhydride; tetrachlorophthalic acid anhydride; endomethylene tetrahydrophthalic acid anhydride; glutaric acid anhydride; maleic acid; maleic acid anhydride; fumaric acid; dimeric and trimeric fatty acids such as oleic acid which may be mixed with monomeric fatty acids; dimethyl terephthalate; terephthalic acid-bis-glycol esters and any mixtures thereof. The following are examples of suitable diols: Ethylene glycol; propylene glycol-(1,2) and -(1,3); butylene glycol-(1,4) and -(2,3); hexanediol-(1,6); octanediol-(1,8); neopentyl glycol: cyclohexane dimethanol (1,4-bis-hydroxymethyl-cyclohexane); 2-methyl-1,3-propanediol; the butene-diol isomers; diethylene glycol; triethylene glycol; tetraethylene glycol; polyethylene glycols; dipropylene glycol; polypropylene glycols; dibutylene glycol and polybutylene glycols.

The preferred acid components are malonic acid and its esters, maleic acid anhydride, maleic acid and its esters, fumaric acid and its esters and muconic acid and its esters.

The preferred diols are ethanediol, propanediol and the polycondensates thereof, preferably those with a molecular weight up to 400, butenediols, butanediols and mixtures of these diols.

The reaction initiators used for the reaction of the polyesters with phospholine, phospholane or phosphetane oxides containing double bonds may be radical forming agents which are active at temperatures within the range of about 50° C. to 300° C., particularly organic peroxides and aliphatic azo compounds as well as high energy radiation. The following are examples: Dialkylperoxides such as di-tert.-butylperoxide; diacylperoxides such as dibenzoyl peroxide, p-chloro-benzoylperoxide, 2,4-dichlorobenzoylperoxide, succinylperoxide, nonanoylperoxide, lauroylperoxide; peroxyesters such as tert.-butyl peroxtoate, tert.-butyl perisobutyrate, tert.-butylperacetate, tert.-butyl perbenzoate, tert.-butylperpivalate, peroxyketals, percarbonates, azoisobutyric acid nitrile and azo-bis-isobutanoldiacetate as well as UV radiation, X-rays and gamma rays.

Polyester based catalysts used according to the instant invention may also be prepared by replacing part of the diol components used in the known method of preparing polyesters by dihydroxyalkyl substituted phospholine oxides or phospholane oxides of the kind described above (formulae III, IV and VII).

The low molecular weight carbodiimidization catalysts may, of course, also be built into other polycondensation or polyaddition resins via suitable functional groups (e.g. OH, $NH_2$ or COOH) in a similar manner, for example into polyamides, polyurethanes or epoxide resins.

There are various possibilities of preparing the high molecular weight catalysts used according to the invention by incorporating low molecular weight carbodiimidization catalysts into polystyrene, and preferably cross-linked polystyrene. Thus, for example, one of the compounds of formula I, III, V, VI or VIII may be copolymerized with styrene and optionally also about 1 to 10% by weight of divinylbenzene with the aid of the above mentioned reaction initiators.

Another method consists of metallizing a halogenated polystyrene (see Houben-Weyl XIV/2,764 (1963)) (preferably with the aid of tertiary butyl lithium) and then reacting it with halogenated phospholine oxides or phospholane oxides, preferably with 1-chloro-phospholine oxides.

Alternatively, phospholine oxides (preferably 1-methyl-1-phospha-2- or -3-cyclopentene-1-oxide) may be added to a matrix which has anionic groups (e.g. alcoholate groups on a polyvinyl alcohol) by a similar method to that described above for the preparation of compounds of the formula (V).

Suitable catalysts may also be prepared using polymers which have been functionalized with $PX_2$ groups (X=Cl,Br), e.g. copolymers of styrene and divinylbenzene (see for example Houben-Weyl XIV/1, page 821 (1961)). The catalytically active phospholine ring is formed by addition of 1,3-dienes, e.g. 1,3-butadiene, isoprene or 2,3-dimethyl-1,3-butadiene (see reaction scheme X) on the phosphorus atom.

Compounds of formula I, III or VIII which may contain substituents with olefinic C-C double bonds or compounds of the formula $R-PX_2$ (X=Cl, Br) in which R is an alkenyl group may, of course, also be polymerized with other olefinically unsaturated monomers (e.g. ethylene, propylene, butene, butadiene, vinyl chloride, vinyl acetate and N-vinylpyrrolidone) and may be built into a high molecular weight matrix in this way.

Catalysts suitable for the purpose of the invention may also be obtained by, for example, heating a phospholine halide of formula (VIII), which may be saturated, with high molecular weight polyhydroxyl compounds, e.g. polyvinyl alcohols, optionally in the presence of bases and with catalytic quantities of alkyl halides. The catalytically active phospholine oxide is then obtained on the matrix by linkage of an additional carbon-phosphorus bond in accordance with reaction scheme (IX) (U.S. Pat. No. 3,723,520; Houben-Weyl, XII/1, page 150 (1963)).

The catalysts described above are in principle capable of effecting carbodiimidization of any aliphatic, cycloaliphatic, araliphatic, aromatic or heterocyclic polyisocyanates such as those described, for example, by W. Siefken in Justus Liebigs Annalen der Chemie, 562, pages 75 to 136. Specific examples include ethylene diisocyanate; tetramethyl-1,4-diisocyanate; hexamethylene-1,6-diisocyanate; dodecane-1,12-diisocyanate; cyclobutane-1,3-diisocyanate; cyclohexane-1,3- and -1,4-diisocyanate and any mixtures of these isomers; 1-isocyanato-3,3,5-trimethyl-5-isocyanatomethylcyclohexane (German Auslegeschrift No. 1,202,785; U.S. Pat. No. 3,401,190); hexahydrotolylene-2,4- and -2,6-diisocyanate and any mixtures of these isomers; hexahydrophenylene-1,3- and/or 1,4-diisocyanate; perhydrodiphenylmethane-2,4' and/or -4,4'-diisocyanate; phenylene-1,3- and -1,4-diisocyanate; tolylene-2,4- and -2,6-diisocyanate and any mixtures of these isomers; diphenylmethane-2,4' and/or 4,4'-diisocyanate; naphthylene-1,5-diisocyanate; triphenylmethane -4,4',4"-triisocyanate; polyphenyl-polymethylene-polyisocyanates which can be obtained by aniline formaldehyde condensation followed by phosgenation and which have been described e.g. in British Patent Specification Nos. 874,430 and 848,671; m- and p-isocyanatophenylsulphonylisocyanates according to U.S. Pat. No. 3,454,606; perchlorinated arylpolyisocyantes of the kind described e.g. in German Auslegeschrift No. 1,157,601 (U.S. Pat. No. 3,227,138); polyisocyanates with carbodiimide groups as described in German Patent Specification No. 1,092,007 (U.S. Pat. No. 3,152,162); the diisocyanates described in U.S. Pat. No. 3,492,330; polyisocyanates with allophanate groups as described e.g. in British Patent Specification No. 994,890; Belgian Patent Specification No. 761,626 and published Dutch Patent Application No. 7,102,524; polyisocyanates with isocyanurate groups as described e.g. in U.S. Pat. No. 3,001,973; German Patent Specification Nos. 1,022,789; 1,222,067 and 1,027,394 and in German Offenlegungsschriften Nos. 1,929,034 and 2,004,048; polyisocyanates with urethane groups as described e.g. in Belgian Patent Specification No. 752,261 or U.S. Pat. No. 3,394,164; polyisocyanates with acylated urea groups according to German Patent Specification No. 1,230,778; polyisocyanates with biuret groups as described e.g. in German Patent Specification No. 1,101,394 (U.S. Pat. Nos. 3,124,605 and 3,201,372) and British Patent Specification No. 889,050; polyisocyanates prepared by telomerization reactions as described e.g. in U.S. Pat. No. 3,654,106; polyisocyanates with ester groups such as those mentioned e.g. in British Patent Specification Nos. 965,474 and 1,072,956, U.S. Pat. No. 3,567,763 and in German Patent Specification No. 1,231,688; reaction products of the above mentioned isocyanates with acetals according to German Patent Specification No. 1,072,385 and polyisocyanates containing polymeric fatty acid groups according to U.S. Pat. No. 3,455,883.

The distillation residues obtained from the commercial production of isocyanates and still containing isocyanate groups may also be used, optionally dissolved in one or more of the above mentioned polyisocyanates. Any mixtures of the above mentioned polyisocyanates may also be used.

The following aromatic polyisocyanates are preferred according to the invention: Tolylene-2,4-diisocyanate; tolylene-2,6-diisocyanate and any mixtures of these isomers; 4,4'-diisocyanatodiphenylmethane; p-phenylene-diisocyanate and approximately 10 to 40% by weight solutions of biuretization, allophanatization, urethanization, trimerization and dimerization products of these polyisocyanates in monomeric polyisocyanates, in particular in monomeric tolylene diisocyanates.

Among the aliphatic, cycloaliphatic and araliphatic polyisocyanates, the following are preferred: Tetramethylene diisocyanate; pentamethylene diisocyanate; hexamethylene diisocyanate; dicyclohexylmethane diisocyanate; 1-isocyanato-3,3,5-trimethyl-5-isocyanatomethylcyclohexane; lysine ester diisocyanates; m- and p-xylylene diisocyanate and mixtures thereof and solutions of their biuretization and dimerization products in the appropriate monomeric polyisocyanates.

Monoisocyanates can of course also be carbodiimidized. Suitable monoisocyanates include e.g.: methylisocyanate; ethylisocyanate; propylisocyanate; isopropylisocyanate; diisopropylphenylisocyanate; n-butylisocyanate; n-hexylisocyanate; ω-chlorohexylisocyanate; phenylisocyanate; tolylisocyanate; p-chlorophenylisocyanate; 2,4-dichlorophenylisocyanate and trifluoromethylphenylisocyanate.

Carbodiimidization of these mono- and polyisocyanates and mixtures thereof is carried out by bringing the isocyanates (if desired as solutions in inert solvents such as toluene, xylene, chlorobenzene, o-dichlorobenzene, decaline, dimethylformamide, dimethylacetamide, butyl acetate, carbon tetrachloride, trichloroethylene or tetramethylurea) into contact with preferably 0.2 to 10% by weight and most preferably 1 to 4% by weight, based on the isocyanate, of matrix charged with catalytically active centers at temperatures between about 50° and 200° C., and preferably 80° to 185° C., and optionally under pressure. This is most simply carried out by stirring the catalyst into liquid or dissolved isocyanates and then removing it by decanting or filtration when the desired degree of carbodiimidization has been reached. The degree of conversion can easily be followed by measuring the volume of carbon dioxide evolved during the carbodiimidization reaction. The catalysts used in the process according to the invention can generally be used more than 10 to 20 times without loss of activity. Carbodiimidization may, of course, also be carried out continuously in a reaction column if provision is made for the free escape of all the carbon dioxide formed in the reaction.

The carbodiimidized or only partially carbodiimidized monoisocyanates and/or polyisocyanates prepared according to the invention may, of course, be subsequently mixed with further quantities of polyisocyanates. In this way it is possible to obtain storage-stable mixtures of high molecular weight and/or low molecular weight polyisocyanates with high molecular weight and/or low molecular weight carbodiimides and uretoneimines which may contain isocyanate groups.

Since, in contrast to the catalysts previously known, the carbodiimidization catalysts used according to the invention can be completely removed after the reaction it is in principle possible to prepare mixtures with any carbodiimide group content but according to the invention, the mixtures preferably contain about 3 to 100% by weight and most preferably 10 to 100% by weight of carbodiimides or polycarbodiimides and uretoneimines thereof. As is well known in the art, uretoneimines are addition compounds of a carbodiimide and an isocyanate. The following polyisocyanate/carbodiimide mixtures are particularly important technically:

(a) Partially (to an extent of 5 to 60%, preferably 10 to 50%) carbodiimidized mixtures of hexamethylenediisocyanate and 1-isocyanato-3,3,5-trimethyl-5-isocyanatomethylcyclohexane (molar ratio in which the diisocyanates are mixed: between 0.1:1 and 10:1, preferably between 0.5:1 and 2:1);

(b) Partially (to an extent of 5 to 70%, preferably 10 to 60%) carbodiimidized 4,4'-diisocyanatodiphenylmethane or tolylene diisocyanate;

(c) Mixture of 100 parts by weight of 4,4'-diisocyanatodiphenyl methane and/or 1,5-naphthylene diisocyanate and 5 to 150 parts by weight of an equilibrium mixture of diisocyanatocarbodiimides of tolylene diisocyanate and of the corresponding triisocyanatouretoneimines;

(d) Mixtures of 100 parts by weight of 4,4'-diisocyanatodiphenylmethane and/or 1,5-naphthylene diisocyanate and 10 to 30 parts by weight of an equilibrium mixture of carbodiimides of phenyl isocyanate, hexamethylene diisocyanate, tetramethylene diisocyanate, cyclohexyl isocyanate or tolylisocyanate and the uretoneimines thereof;

(e) Mixtures of 100 parts by weight of tolylene diisocyanate and 5 to 30 parts by weight of an equilibrium mixture of carbodiimidized phenyl isocyanate or tolylisocyanate and their uretoneimines;

(f) Mixture of 100 parts by weight of modified tolylene diisocyanate containing 10 to 40% by weight of biuret, allophanate, urethane or isocyanurate polyisocyanates based on tolylene diisocyanate and from 10 to 20 parts by weight of an equilibrium mixture of tolyene diisocyanatocarbodiimide and the corresponding triisocyanatouretoneimine;

(g) Mixture of 100 parts by weight of biuret polyisocyanates of hexamethylene diisocyanate (preferably the reaction products of 1 mol of water and about 2 to 3 mol of hexamethylene diisocyanate) and from 10 to 150 parts by weight of an equilibrium mixture of the carbodiimide of hexamethylene diisocyanate and the corresponding uretoneimine polyisocyanates;

(h) Mixtures of 100 parts by weight of $\alpha,\omega$-diisocyanato prepolymers (based on $\alpha,\omega$-dihydroxypolyesters of polyethers and from 1.4 to 2.5 mol, preferably 1.6 to 2 mol of tolylene diisocyanate) diisocyanatodiphenylmethane or hexamethylene diisocyanate and from 5 to 30 parts by weight of an equilibrium mixture of carbodiimides or carbodiimide diisocyanates and the corresponding uretoneimine polyisocyanates of phenyl isocyanate, tolyl isocyanate, tetramethylene diisocyanate, hexamethylene diisocyanate or tolylene diisocyanate.

The carbodiimides prepared according to the invention, which may contain isocyanate groups, and solutions of these carbodiimides in polyisocyanates which are free from carbodiimide groups, are valuable starting materials for the diisocyanate polyaddition process and may be used for the production of various hard to elastic and optionally cellular synthetic resins used for the manufacture of lacquers, coatings, foils and shaped products. Polyurethanes produced in this way contain carbodiimide groups and uretoneimine groups (masked carbodiimide groups) firmly built into the polymer molecule. These groups at the same time serve as age resistors against the hydrolysis of ester bonds and reduce the flammability of the synthetic resins.

Preparation of the polyurethanes is carried out by the known method of reacting polyisocyanate mixtures with high molecular weight and, optionally, also low molecular weight compounds which have at least two hydrogen atoms capable of reacting with isocyanates.

The compounds having at least two hydrogen atoms reactive with isocyanates may be compounds having amino groups, thiol groups or carboxyl groups but are preferably polyhydroxy compounds in particular compounds with from two to eight hydroxyl groups, and especially those with a molecular weight of from 400 to 10,000 and preferably 800 to 6000, e.g. polyesters, polyethers, polythioethers, polyacetals, polycarbonates and polyester amides having at least two generally two to eight but preferably two to four hydroxyl groups, such as compounds of this kind known per se for the production of both homogeneous and cellular polyurethanes.

Suitable polyesters with hydroxyl groups include e.g. reaction products of polyhydric, preferably dihydric alcohols to which trihydric alcohols may be added and polybasic, preferably dibasic carboxylic acids. Instead of using free polycarboxylic acids, the corresponding polycarboxylic acid anhydrides or polycarboxylic acid esters of lower alcohols or mixtures thereof may be used for preparing the polyesters. The polycarboxylic acids may be aliphatic, cycloaliphatic, aromatic and/or heterocyclic and they may be substituted, e.g. with halogen atoms, and/or unsaturated. The following are examples of such acids: Succinic acid; adipic acid; suberic acid; azelaic acid; sebacic acid; phthalic acid; isophthalic acid; trimellitic acid; phthalic acid anhydride; tetrahydrophthalic acid anhydride; hexahydrophthalic acid anhydride; tetrachlorophthalic acid anhydride; endomethylene tetrahydrophthalic acid anhydride; glutaric acid anhydride; maleic acid; maleic acid anhydride; fumaric acid; dimeric and trimeric fatty acids such as oleic acid which may be mixed with monomeric fatty acids; dimethylterephthalate and terephthalic acid-bis-glycol esters. Suitable polyhydric alcohols include e.g. ethylene glycol; propylene glycol-(1,2) and -(1,3), butylene glycol-(1,4) and -(2,3); hexanediol-(1,6); octanediol-(1,8); neopentylglycol; cyclohexanedimethanol (1,4-bis- hydroxymethylcyclohexane); 2-methyl-1, 3-propanediol; glycerol; trimethylolpropane; hexane-1,2,6-triol; butane-1,2,4-triol; trimethylolethane; pentaerythritol; quinitol; mannitol and sorbitol; methyl glycoside; diethylene glycol; triethylene glycol; tetraethyleneglycol; polyethylene glycols; dipropylene glycol; polypropylene glycols; dibutylene glycol and polybutylene glycols. The polyesters may also contain a proportion of carboxyl end groups. Polyesters of lactones such as $\epsilon$-caprolactone or hydroxycarboxylic acids such as $\omega$-hydroxycaproic acid may also be used.

The polyethers used according to the invention which contain at least two, generally two to eight and preferably two to three hydroxyl groups are known per se and can be prepared e.g. by the polymerization of epoxides such as ethylene oxide; propylene oxide; butylene oxide; tetrahydrofuran; styrene oxide or epichlorohydrin, either each on its own, e.g. in the presence of boron trifluoride, or by addition of these epoxides, either as mixtures or successively, to starting components with reactive hydrogen atoms such as water, alcohols or amines, e.g. ethylene glycol; propylene glycol-(1,3) or -(1,2); trimethylolpropane; 4,4'-dihydroxy-diphenylpropane; aniline, ammonia, ethanolamine or ethylene diamine. Sucrose polyethers such as those mentioned in Auslegeschriften Nos. 1,176,358 and 1,064,938, for example, may also be used according to the invention. It is in many cases preferred to use polyethers which contain predominantly primary hydroxyl groups (up to 90% by weight, based on all the hydroxyl groups present in the polyether). Polyethers modified with vinyl polymers, e.g. the compounds obtained by polymerization of styrene and acrylonitrile in the presence of polyethers as described in U.S. Pat. Nos. 3,383,351; 3,304,273; 3,523,093 and 3,110,695 and German Patent Specification No. 1,152,536 and polybutadienes containing hydroxyl groups are also suitable.

Suitable polythioethers include, in particular, the condensation products obtained from thiodiglycol on its own and/or by reaction with other glycols, dicarboxylic acids, formaldehyde, aminocarboxylic acids or aminoalcohols. The products obtained are polythio mixed ethers, polythio ether esters or polythioether ester amides, depending on the cocomponents.

Suitable polyacetals include e.g. the compounds which can be prepared from glycols such as diethyleneglycol; triethyleneglycol; 4,4'-dioxethoxy-diphenyldimethylmethane or hexanediol and formaldehyde. Suitable polyacetals for the purpose of the invention may also be prepared by the polymerization of cyclic acetals.

Suitable polycarbonates with hydroxyl groups are known per se and can be prepared e.g. by the reaction of diols such as propane-1,3-diol; butane-1,4-diol and/or hexane-1,6-diol or diethylene glycol; triethylene glycol or tetraethylene glycol with diarylcarbonates such as diphenylcarbonate or phosgene.

Suitable polyester amides and polyamides include e.g. the predominantly linear condensates obtained from polyvalent saturated and unsaturated carboxylic acids or their anhydrides and polyvalent saturated and unsaturated amino alcohols, diamines, polyamines and mixtures thereof.

Polyhydroxyl compounds already containing urethane or urea groups and modified or unmodified natural polyols such as castor oil, carbohydrates or starch may also be used. Addition products of alkylene oxides and phenol formaldehyde resins or of alkylene oxides and urea formaldehyde resins are also suitable according to the invention.

Representatives of these compounds which may be used according to the invention have been described, for example in High Polymers, Vol. XVI, "Polyurethanes, Chemistry and Technology", by Saunders-Frisch, Interscience Publishers, New York, London, Volume I, 1962, pages 32 to 42 and pages 44 to 54 and Volume II, 1964, pages 5 to 6 and 198 to 199 and in KunststoffHandbuch, Volume VII, Vieweg-Hochtlen, Carl-Hanser-Verlag, Munich, 1966, e.g. on pages 45 to 71.

Mixtures of the above mentioned compounds having at least two hydrogen atoms capable of reacting with isocyanates and a molecular weight of 400 to 10,000 may of course also be used, e.g. mixtures of polyethers and polyesters.

The starting components used according to the invention may, if desired, also include compounds with a molecular weight of 32 to 400 which contain at least two hydrogen atoms capable of reacting with isocyanates. These compounds again are compounds containing hydroxyl groups and/or amino groups and/or thiol groups and/or carboxyl groups, preferably hydroxyl groups and/or amino groups. They are used as chain-lengthening agents or cross-linking agents. They generally have from two to eight hydrogen atoms capable of reacting with isocyanates, preferably two or three such hydrogen atoms. The following are examples of such compounds: Ethylene glycol; propylene glycol-(1,2) and -(1,3); butylene glycol-(1,4) and -(2,3); pentane-1,5-diol; hexane-1,6-diol; octane-1,8-diol; neopentylglycol; 1,4-bis-hydroxymethyl-cyclohexane; 2-methyl-1,3-propanediol; glycerol; trimethylolpropane; hexane-1,2,6-triol; trimethylol-ethane; pentaerythritol; quintol, mannitol and sorbitol; diethyleneglycol; triethyleneglycol; tetraethylene glycol; polyethylene glycols with a molecular weight of up to 400; dipropylene glycol; polypropylene glycols with a molecular weight of up to 400, dibutylene glycol; polybutylene glycols with a molecular weight of up to 400; 4,4'-dihydroxy-diphenylpropane; dihydroxymethylhydroquinone; ethanolamine; diethanolamine; triethanolamine; 3-aminopropanol; ethylenediamine; 1,3-diaminopropane; 1-mercapto-3-aminopropane; 4-hydroxyphthalic acid; 4-aminophthalic acid; succinic acid; adipic acid; hydrazine; N,N'-dimethylhydrazine and 4,4'-diaminodiphenyl methane.

Here again, mixtures of various compounds having a molecular weight of from 32 to 400 and containing at least two hydrogen atoms which are reactive with isocyanates may be used.

If the polyisocyanate mixtures according to the invention which contain carbodiimide groups are to be used for the production of foams, water and/or readily volatile organic substances are used as blowing agents, for example acetone, ethyl acetate, halogen substituted alkanes such as methylene chloride, chloroform, ethylidene chloride, vinylidene chloride, monofluorotrichloromethane, chlorodifluoromethane or dichlorodifluoromethane or butane, hexane, heptane or diethylether. The effect of a blowing agent can also be obtained by the addition of compounds which decompose at temperatures above room temperature to liberate gases such as nitrogen, e.g. azo compounds such as azo isobutyric acid nitrile. Other examples of blowing agents and details concerning the use of blowing agents may be found in Kunststoff-Handbuch, Volume VII, published by Vieweg and Hochtlen, Carl-Hanser-Verlag, Munich, 1966, e.g. on pages 108 and 109, 453 to 455 and 507 to 510.

Additional catalysts are often used with the carbodiimidized polyisocyanate mixtures according to the invention. These include catalysts known per se, e.g. tertiary amines such as triethylamine; tributylamine; N-methylmorpholine; N-ethylmorpholine; N-cocomorpholine; N,N,N',N'-tetramethylethylenediamine; 1,4-diaza-bicyclo-(2,2,2)-octane; N-methyl-N'-dimethylaminoethyl-piperazine; N,N-dimethylbenzylamine; bis-(N,N-diethylaminoethyl)-adipate; N,N-diethylbenzylamine; pentamethyldiethylene-triamine; N,N-dimethylcyclohexylamine; N,N,N',N'-tetramethyl-1,3-butanediamine; N,N-dimethyl-$\beta$-phenylethylamine; 1,2-dimethylimidazole or 2-methylimidazole. The known Mannich bases of secondary amines such as dimethylamine and aldehydes, preferably formaldehyde, or ketones such as acetone, methyl ethyl ketone or cyclohexanone and phenols such as phenol, nonylphenol or bisphenol may also be used as catalyst.

Tertiary amines with isocyanate reactive hydrogen atoms which may be used as catalysts include e.g. triethanolamine, triisopropanolamine, N-methyldiethanolamine, N-ethyldiethanolamine, N,N-dimethyl-ethanolamine and their reaction products with alkylene oxides such as propylene oxide and/or ethylene oxide.

Silaamines with carbon-silicon bonds may also be used as catalysts, e.g. the compounds described in German Patent Specification No. 1,229,290 corresponding to U.S. Pat. No. 3,620,984 such as 2,2,4-trimethyl-2-silamorpholine and 1,3-diethylaminomethyl-tetramethyl-disiloxane.

Basic nitrogen compounds such as tetraalkylammonium hydroxides, alkali metal hydroxides such as sodium hydroxide, alkali metal phenolates such as sodium phenolate and alkali metal alcoholates such as sodium methylate may also be used as catalysts. Hexahydrotriazines are also suitable catalysts.

Organic metal compounds may also be used as catalysts, particularly organic tin compounds.

The organic tin compounds used as catalysts are preferably tin(II) salts of carboxylic acids such as tin(II) acetate, tin(II) octoate, tin(II) ethylhexoate and tin(II) laurate and the compounds of tetravelent tin such as dibutyl tin oxide, dibutyl tin dichloride, dibutyl tin diacetate, dibutyl tin dilaurate, dibutyl tin maleate or dioctyl tin diacetate. Any of the above mentioned catalysts may, of course, be used as mixtures.

Other examples of suitable catalysts and details concerning the activity of the catalysts may be found in Kunststoff-Handbuch, Volume VII, published by Vieweg and Hochtlen, Carl-Hanser-Verlag, Munich 1966, e.g. on pages 96 to 102.

Surface active additives such as emulsifiers and foam stabilizers may also be used in the production of the foams. Suitable emulsifiers include e.g. the sodium salts of ricinoleic sulphonates and salts of fatty acids with amines such as oleic acid diethylamine or stearic acid diethanolamine. Alkali metal or ammonium salts of sulphonic acids such as dodecylbenzene sulphonic acid or dinaphthylmethane disulphonic acid or of fatty acids such as ricinoleic acid or of polymeric fatty acids may also be used as surface active additives.

The foam stabilizers used are mainly polyether siloxanes, especially those which are water-soluble. These compounds generally have a polydimethylsiloxane group attached to a copolymer of ethylene oxide and propylene oxide. Foam stabilizers of this kind have been described, for example, in U.S. Pat. Nos. 2,834,748; 2,917,480 and 3,629,308.

Other additives which may also be used include reaction retarders, e.g. compounds which are acid in reaction such as hydrochloric acid or organic acid halides, cell regulators known per se such as paraffins or fatty alcohols or dimethyl polysiloxanes, pigments, dyes, flame retarding agents known per se such as tris-chloroethylphosphate. Tricresylphosphate and ammonium phosphate and polyphosphate, stabilizers against ageing and weathering, plasticizers, fungistatic and bacteriostatic substances and fillers such as barium sulphate, kieselguhr, carbon black or whiting.

Other examples of surface active additives, foam stabilizers, cell regulators, reaction retarders, stabilizers, flame retarding additives, plasticizers, dyes, fillers and fungistatic and bacteriostatic substances which may also be used and the use and action of such additives have been described in Kunststoff-Hanbuch, Volume VII, published by Vieweg and Hochtlen, Carl-Hanser-Verlag, Munich, 1966, e.g. on pages 103 to 113.

When used in a process according to the invention, the polyisocyanate mixtures containing carbodiimide groups are reacted by the known one-shot prepolymer or semiprepolymer process. Mechanical devices are often used, e.g. those described in U.S. Pat. No. 2,764,565. Suitable processing apparatus have been described in Kunststoff-Handbuch, Volume VII, published by Vieweg and Hochtlen, Carl-Hanser-Verlag, Munich, 1966 e.g. on pages 121 to 205.

Production of the foams is in many cases carried out inside molds. The process consists of introducing the reaction mixture into a mold made of a metal such as aluminum or a synthetic resin such as an epoxide resin. The foamable reaction mixture foams up inside the mold to form the shaped product. This process of foaming in a mold may be carried out to produce a product having a cellular structure on its surface or it may be carried out to produce a product with a non-cellular skin and cellular center. According to the invention, one or other result may be obtained by either introducing just sufficient foamable reaction mixture into the mold to fill the mold with foam after the reaction or introducing a larger quantity of reaction mixture than is necessary for filling the mold with foam. The latter method is known as overcharging, a procedure which has already been disclosed, e.g. in U.S. Pat. Nos. 1,178,490 and 3,182,104.

When foaming is carried out inside molds, so-called external mold release agents such as silicone oils are frequently used, but so-called internal mold release agents may also be used, optionally as mixtures with external mold release agents, e.g. those disclosed in German Offenlegungsschriften Nos. 2,121,670 and 2,307,589.

Foams may, of course, also be produced by foaming in a block or by the known laminater process.

The following Examples serve to explain the present invention.

The figures given represent parts by weight or percent-agents by weight unless otherwise indicated.

EXAMPLE 1

(a) 70 parts by weight of a polyester with an acid number of about 8 (prepared from 406 parts by weight of maleic acid anhydride and 438 parts by weight of diethylene glycol) were slowly heated to 150° C. with 30 parts by weight of 1-methyl-1-phospha-2 and 3-cyclopentene-1-oxide (1-methylphospholine oxide) in the presence of 1.5 g of benzoyl peroxide with stirring. A soft, crumbly product was already obtained at 110° C. After extraction of residual monomers, first with toluene and then with chloroform, the polymer contained 1.25 percent by weight of phosphorus.

(b) Example 1a was repeated but with the addition of 3.5 parts by weight of styrene to the reaction mixture. A slightly harder product with a phosphorus content of 0.5% by weight was obtained.

25 Parts by weight of the catalyst from Example 1a and 40 parts by weight of toluene were added to 34.8 parts by weight of an isomeric mixture of 2,4- and 2,6-tolylene diisocyanate (80:20) and the mixture was heated to 110° C. 3.6 liters of carbon dioxide had evolved after one hour and the isocyanate content of the solution of isocyanate mixture had dropped to 8.6% by weight.

EXAMPLE 2

(a) 35 Parts by weight of an unsaturated polyester (of 1 mol of maleic acid anhydride and 1 mol of tetraethylene glycol) with an acid number of 9 were vigorously mixed with 15 parts by weight of 1-methyl-1-phospha-3-cyclopenten-1-oxide and 0.75 parts by weight of benzoyl peroxide and the mixture was slowly heated to 150° C. with stirring.

When the crumbly product thereby obtained had been washed with toluene and chloroform, it was found to have a phosphorus content of 0.75 percent by weight.

(b) When Example 2a was repeated, using 1-methyl-1-phospha-2-cyclopentene-1-oxide instead of 1-methyl-1-phospha-3-cyclopentene-1-oxide, the phosphorus content of the reaction product was found to be 0.2 percent by weight.

EXAMPLE 3

14 Parts by weight of the unsaturated polyester from Example 2 were mixed with 6 parts by weight of 1-allyl-1-phospha-2 and 3-cyclopentene-1-oxide and 0.3 parts by weight of benzoyl peroxide and slowly heated to 150° C. with stirring. A crumbly product was obtained, which had a phosphorus content of 2.7 percent by weight after extraction with toluene and chloroform.

When 5 parts by weight of the catalyst were heated to 90° C. with 150 parts by weight of a mixture of 2,4-and 2,6-tolylene diisocyanate (80:20) carbodiimidization took place, accompanied by the evolution of 3 liters of carbon dioxide over a period of one hour.

EXAMPLE 4

9.8 Parts by weight of maleic acid anhydride and 5.2 parts by weight of diethylene glycol were heated to 175° C. with 25.6 parts by weight of a diester of an isomeric mixture of 1-methyl-2 - and 3-phosphoric acid phospholane oxide and polypropylene glycol (molecular weight 511) under an atmosphere of nitrogen, and the water formed in the esterification reaction was distilled off. The gel-like product was mixed with 0.6 parts by weight of benzoyl peroxide and heated to 150° C. Soluble components were removed from the resulting crumbly product by extraction with toluene and chloroform.

When 1 part by weight of the catalyst was heated to 110° C. with 34.8 parts by weight of a mixture of 2,4- and 2,6-tolylene diisocyanate (80:20), 2 liters of carbon dioxide were evolved over a period of 10 minutes.

EXAMPLE 5

9.8 Parts by weight of maleic acid anhydride were condensed for 3 hours at 175° C. under an atmosphere of nitrogen with 9 parts by weight of diethylene glycol and 3.7 parts by weight of a product obtained by heating 1 mol of 1-methyl-phospholan-2 and 3-phosphonic acid dimethyl ester with 2 mol of diethanolamine. The water formed in the reaction was continuously distilled off and the condensate was subsequently treated with toluene and chloroform to remove residues of soluble components. The resulting product had a phosphorus content of 0.6% by weight.

1 Part by weight of this product was heated to 190° C. with 84 parts by weight of hexamethylene diisocyanate. 2 liters of carbon dioxide were evolved over a period of 5 hours.

10 Parts by weight of the product were heated to 70° C. with 174 parts by weight of a mixture of 2,4- and 2,6-tolylene diisocyanate. 10 liters of carbon dioxide were evolved over a period of 30 minutes as a result of carbodiimidization of the isocyanate.

EXAMPLE 6

7.1 Parts by weight of a 2% by weight solution of poly-p-iodostyrene in toluene were added dropwise at 0° C. to 150 ml (0.22 mol) of a solution of n-butyl lithium in toluene. 35.5 parts by weight of 1-chloro-3-methyl-1-phospha-2 and 3-cyclopentene-1-oxide were then rapidly added at 20° C. 5 ml of water were added to the reaction mixture after one hour's stirring and the mixture was concentrated by evaporation, digested with a small quantity of water and dehydrated over phosphorus pentoxide in a desiccator.

Tolylene diisocyanate could be carbodiimidized at a temperature of only 60° C. with the aid of the resulting highly active catalyst.

EXAMPLE 7

15 Parts by weight of poly-p-iodostyrene cross-linked with 2% of divinylbenzene were left to swell in 100 ml of toluene. 200 ml of a 1.5 normal solution of n-butyl lithium in n-hexane were added dropwise. The solid metallized product obtained was suction filtered under nitrogen and reacted at room temperature with 9.7 parts by weight of 3-chloro-1-methyl-1-phospha-2 and 3-cyclopentene-1-oxide prepared from chloroprene and dichloromethylphosphine. The product was filtered off and treated with toluene and chloroform.

Tolylene diisocyanate could be carbodiimidized at 100° C. with the aid of this catalyst.

EXAMPLE 8

268 Parts by weight of phosphorus trichloride were added to 50 parts by weight of polystyrene and the mixture was reacted for 5 days at 200° C. (see also U.S. Pat. No. 2,844,546). Excess phosphorus trichloride was then distilled off. The residue was taken up with perchloroethylene three times and the solvent was distilled off in each case. 190 Parts by weight of isoprene and 0.6 parts by weight of ionol were added to this purified solid product under an atmosphere of nitrogen and the mixture was left to stand at room temperature for 10 days. The solid product was washed with perchloroethylene, hydrolyzed with 1 liter of ice water, suction filtered and dehydrated over phosphorus pentoxide.

34.8 Parts by weight of an isomeric mixture of 2,4- and 2,6-tolylenediisocyanate (80:20) were carbodiimidized with 3 parts by weight of the catalyst at 140° C. 1 liter of carbon dioxide was evolved over a period of one hour during this reaction.

EXAMPLE 9

A mixture of
3 parts by weight of polystyrene (average molecular weight 30000),
6 parts by weight of styrene,
1 part by weight of 1-allyl-phospholine oxide (1-allyl-1-phospha-2 and 3-cyclopentene-1-oxide), prepared from equivalent parts of 1-chloro-phospholine oxide (1-chloro-1-phospha-2 and 3-cyclopentene-1-oxide) and allyl magnesium iodide in tetrahydrofuran,
0.6 parts by weight of divinyl benzene and
0.008 parts by weight of dibenzoyl peroxide
was introduced into a bomb tube under an atmosphere of nitrogen. The solid product was grated after 30 days at 32° C. and freed from residues of soluble components with the aid of toluene and chloroform. The phosphorus content of the product was 0.3% by weight.

Tolylene diisocyanate was converted into the carbodiimide at 75° C. under the action of this catalyst.

EXAMPLE 10

9 Parts by weight of styrene and 0.1 part by weight of divinylbenzene were mixed with 1 part by weight of 1-methyl-1-phospha-2 and 3-cyclopentene-1-oxide and polymerized at 110° C. using 0.3 parts by weight of benzoyl peroxide as initiator. When the product had been washed with toluene and chloroform, it had a phosphorus content of 1 percent by weight.

EXAMPLE 11

6.8 Parts by weight of 1-chloro-1-phospha-2 and 3-cyclopentene (U.S. Pat. No. 3,723,520) dissolved in 20 parts by weight of dichlorobenzene were added to 2 parts by weight of a polyvinyl alcohol (molecular weight about 15,000) at room temperature. 4 Parts by weight of pyridine were added dropwise, followed by the addition of 0.1 part by weight of ethyl iodide, and the mixture was heated to 110° C. The resulting solid product was suction filtered, washed with water and then with ether and dehydrated over phosphorus pentoxide.

The product was an efficient carbodiimidization catalyst for 2,4- and 2,6-tolylene diisocyanate at a temperature of 150° C. When 2 parts by weight of catalyst were added to 70 parts by weight of a mixture of 2,4- and 2,6-tolylene diisocyanate (80:20), 3 liters of carbon dioxide evolved over a period of 10 minutes at 170° C.

EXAMPLE 12

160 g of diethylmalonate were heated under reflux with 106 g of diethylene glycol and 1 ml of 10% sulphuric acid in 100 ml of toluene for 24 hours and toluene was then slowly distilled off. 240 g of the resulting product were mixed with 240 g of an unsaturated polyester (obtained from equivalent quantities of maleic acid anhydride and diethylene glycol) with an acid number of 8, 206 g of 1-methyl-1-phospha-2 and 3-cyclopentene-1-oxide and 10 g of benzoyl peroxide were added and the mixture was heated to 150° C. The resulting crumbly product had a phosphorus content of 1% after extraction with toluene and chloroform.

When 34.8 g of a mixture of 2,4- and 2,6-tolylene diisocyanate (80:20) were heated to 85° C. with 1 g of the catalyst, 4 liters of carbon dioxide were evolved over a period of 3 hours.

EXAMPLE 13

350 g of an unsaturated polyester with acid number 9 (obtained from equivalent quantities of maleic acid anhydride and tetraethyleneglycol) were mixed with 150 g of 1-methyl-2 and 3-allyloxy-1-phospha-cyclopentane-1-oxide and then slowly heated to 150° C. with stirring together with 7.5 g of benzoyl peroxide and subsequently stirred for a further 30 minutes. The resulting crumbly product was extracted with toluene and with chloroform. The phosphorus content was 2.4%.

EXAMPLE 14

133 g of o-tolylisocyanate and 5 g of solid, insoluble catalyst from Example 1a were heated together to 180° C. with stirring. After the evolution of 12.3 liters of carbon dioxide, which took place within 1.5 hours, the catalyst was suction filtered and the filtrate distilled. 95.3 g of di-o-tolyl-carbodiimide, b.p. 135°–137° C./0.1 Torr were obtained (87% of the theory).

EXAMPLE 15

133 g of o-tolylisocyanate and 5 g of solid, insoluble catalyst from Example 2a were heated to 140° C. with stirring. After evolution of 12.1 liters of carbon dioxide, which took place within 2 hours, the catalyst was suction filtered and the filtrate was distilled. 103.5 g of di-o-tolyl-carbodiimide, b.p. 130°–132° C./0.1 Torr were obtained (94% of the theory).

EXAMPLE 16

203 g of 2,6-diisopropyl-phenylisocyanate and 5 g of catalyst from Example 1a were heated to 200° C. with stirring. After evolution of 8.9 liters of carbon dioxide over a period of 12 hours, the catalyst was suction filtered and the filtrate (177 g) distilled. 132 g of (bis-(2,6-diisopropyl)-phenyl)-carbodiimide, b.p. 165°–168° C./0.1 Torr were obtained (71% of the theory).

EXAMPLE 17

1500 g of a mixture of 2,4- and 2,6-tolylene diisocyanate (80:20) and 50 g of catalyst from Example 2a were heated to 100° C. The product was filtered when 38 liters of carbon dioxide had evolved. It had a viscosity of $\eta_{24}=14$ cP and an isocyanate content of 39%.

EXAMPLE 18

(Comparison Experiment)

When proceeding as described in Example 17 and using 4 parts by weight of phospholine oxide isomers of the following formula

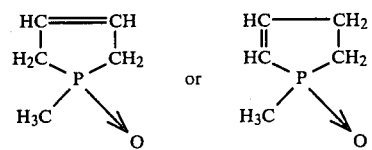

for the formation of isocyanatocarbodiimides and isocyanato polycarbodiimides by a process of homogeneous catalysis, rapid carbodiimide formation already took place at room temperature but the reaction could not be stopped and it was therefore impossible to prepare stable solutions of carbodiimide diisocyanates and the corresponding uretoneimine triisocyanates in excess monomeric polyisocyanate. The resulting solution solidified to a brittle foam after only 2 hours. If, for comparison, 1 to 5% by weight of phosphorus oxychloride, zinc chloride, dimethylcarbamic acid chloride, phosphorus pentachloride and aluminum chloride, boron trifluoride or gaseous hydrogen chloride was added to the solution as inhibitor when about 76 liters of carbon dioxide (determined at 20° C.) had been liberated, subsequent formation of carbodiimide was slowed down but the isocyanate content of the solution continued to fall while the viscosity continued to increase and carbon dioxide continuously evolved. Such solutions cannot be transported in closed vessels and are sources of considerable danger due to the development of high carbon dioxide pressures since the vessels are liable to explode spontaneously.

EXAMPLE 19

The procedure was exactly as described in Example 17 but catalyst 1a already used once was used a second time and the evolution of carbon dioxide was plotted graphically against time. Practically the same shape of curve was obtained as in the first experiment. The catalyst could be used again repeatedly even after the tenth time, provided that care was taken to ensure that, after filtration of the catalyst, any isocyanate adhering thereto was removed by washing with an inert solvent.

EXAMPLE 20

300 g of diphenylmethane-4,4'-diisocyanate and a catalyst according to Example 1a were heated together at 80° to 100° C. After evolution of 3 liters of carbon dioxide, a product which was liquid at room temperature and had an isocyanate content of 29% and a viscosity of $\eta_{24}=46$ cP was obtained.

EXAMPLE 21

168 g of 1,6-hexamethylenediisocyanate and 5 g of catalyst according to Example 13 were heated to 150° C. After the evolution of 14 liters of carbon dioxide, the product was filtered and purified by thin layer evaporation. It then had a viscosity of $\eta_{24}=580$ cP and an isocyanate content of 23%. Gel chromatography showed that more than 80% of the carbodiimide groups had reacted with free isocyanate to form uretoneimine groups.

When applied to a glass plate, the product reacted with atmospheric moisture to form a scratch resistant, elastic film.

EXAMPLE 22

A mixture of 111 parts of weight of 1-isocyanato-3,3,5-trimethyl-5-isocyanatomethyl-cyclohexane and 84 parts by weight of 1,6-hexamethylenediisocyanate was heated to 160° C. and 5 g of a catalyst according to Example 13 were added. When 7.3 liters of carbon dioxide had evolved, the product (viscosity $\eta_{24}=170$ cP) was filtered and thin layered at 80° C./0.12 Torr to remove monomeric isocyanate. The thin layered product contained a high proportion of isocyanatouretoneimines in addition to carbodiimides. The viscosity, $\eta_{24}$ was 916 cP; and the isocyanate content was 23.9%.

EXAMPLE 23

500 g (2 mol) of diphenylmethane-4,4'-diisocyanate were heated to 140° C. with 20 g of the catalyst from Example 1a. When 20 liters of carbon dioxide had been liberated, the resulting isocyanatocarbodiimide which contained uretone imine groups was freed from catalyst by filtration.

The product was stirred in portions of 10, 30 and 50 percent (a, b, c) into molten diphenylmethane-4,4'-diisocyanate. Products which were stable in storage and liquid at room temperature were thereby obtained.

(a) isocyanate content=31% $\eta_{24}=22$ cP
(b) isocyanate content=28% $\eta_{24}=140$ cP
(c) isocyanate content=25.2% $\eta_{24}=1300$ cP

EXAMPLE 24

17.4 g of a mixture of 2,4- and 2,6-tolylene diisocyanate (ratio of isomers 80:20) were added to 225 g of diphenyl methane-4,4'-diisocyanate and carbodiimidized with 5 g of the catalyst from Example 1a at 80° C. After evolution of 1.1 liters of carbon dioxide over a period of 15 minutes, the product was suction filtered. The product finally obtained, which remained liquid at room temperature, had an isocyanate content of 31% and a viscosity of $\eta_{24}=26$ cP.

EXAMPLE 25

100 Parts by weight of a polyol having a hydroxyl number of 28 and an average functionality of 3 (prepared by chemical addition of propylene oxide and ethylene oxide to trimethylol propane used as the starter) 3 parts by weight of water, 4 parts by weight of diisopropanolamine, 1 part by weight of triethanolamine, 0.2 parts by weight of triethylamine, 0.15 part by weight of 1,4-diazabicyclo-(2,2,2)-octane and 1 part by weight of a silicone stabilizer were mixed together. 50.5 parts by weight of the product from Example 17 were added to this mixture and vigorously stirred. A foam with a density of 41 kg/m³ is obtained. According to DIN 53577, its compression resistance of 40% (4.02 k Pascal) was about twice as high as that of a foam produced in a similar manner from an unmodified mixture of 2,4- and 2,6-tolylene diisocyanate (80:20).

What is claimed is:

1. A process for preparing a storage stable, catalyst-free, equilibrium mixture of an organic carbodiimide, an organic uretoneimine and an organic isocyanate comprising the steps:

(a) contacting an organic mono- and/or polyisocyanate with a high molecular weight carbodiimidization catalyst which is insoluble in organic isocyanate and which comprises a high molecular weight, insoluble organic matrix and a low molecular weight carbodiimidization catalyst bound to the matrix via covalent bonds, and (b) removing said high molecular weight catalyst when the desired degree of carbodiimidization has been reached.

2. The process of claim 1, wherein said organic mono- and/or polyisocyanate is dissolved in an inert solvent.

3. The process of claim 1, further comprising the step of:

(c) adding a mono- and/or polyisocyanate which is free of carbodiimide and uretoneimine groups to the equilibrium mixture.

4. The process of claim 1, wherein said matrix is bound to a catalytically active group selected from the group consisting of:

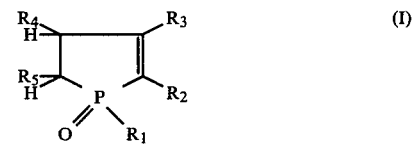

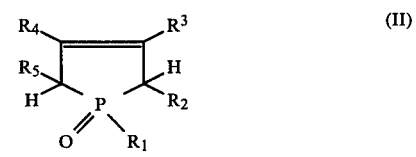

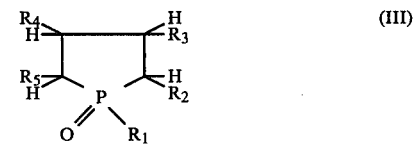

in which $R_1$ represents the organic matrix or an alkyl, aryl or aralkyl group with 1 to 14 carbon atoms and $R_2$, $R_3$, $R_4$ and $R_5$ represent hydrogen, halogen, $C_1-C_{14}$-alkyl, aryl, or aralkyl groups, alkoxy-carbonyl, or phosphonic acid ester groups or $C_1-C_4$-hydroxyalkyl groups or mercaptoalkyl groups or HO.

5. The process of claim 4, wherein said matrix is a polyester resin and wherein said catalytically active groups are bound to the matrix through an ester group, ether group or carbon to carbon bond by way of at least one of the groups $R_1$ to $R_5$ or the phospholane ring is bound directly to the matrix by way of carbon to carbon bonds.

6. The process of claim 4, wherein said matrix is a polystyrene resin and wherein said catalytically active groups are bound to the matrix by way of a least one of the groups $R_1$ to $R_5$ through an ether group or carbon-to-carbon bond or the phospholane ring is bound to the matrix directly by way of a carbon to carbon bond.

7. The process of claim 6, wherein said polystyrene resin is crosslinked with divinyl benzene.

8. The process of claim 4, wherein said matrix is polyvinyl alcohol and wherein $R_1$ represents the polyvinyl alcohol matrix.

9. The process of claim 4, wherein said organic matrix has a molecular weight of at least 2000 and the high molecular weight catalyst has a phosphorous content of from 0.05 to 23 percent by weight.

10. The process of claim 9, wherein from 0.2 to 10 percent by weight of high molecular weight catalyst is used based on the weight of the isocyanate.

* * * * *